United States Patent
Inaba et al.

(10) Patent No.: US 6,197,966 B1
(45) Date of Patent: Mar. 6, 2001

(54) PRODUCTION METHOD OF OPTICALLY ACTIVE AMINO ALCOHOLS

(75) Inventors: Takashi Inaba; Shoichi Sagawa; Hiroyuki Abe, all of Takatsuki (JP)

(73) Assignees: Japan Tobacco Inc., Tokyo (JP); Agouron Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 09/231,639

(22) Filed: Jan. 15, 1999

(30) Foreign Application Priority Data

Jan. 16, 1998 (JP) .................................................. 10-006836

(51) Int. Cl.[7] ...................... C07D 213/18; C07D 211/70; C07D 213/06; C07D 211/92

(52) U.S. Cl. ........................... 546/347; 546/351; 546/352
(58) Field of Search ..................... 549/347, 351, 549/352

(56) References Cited

U.S. PATENT DOCUMENTS

| | | | | |
|---|---|---|---|---|
| 5,635,529 | * | 6/1997 | Dumic et al. ........................ | 549/347 |
| 5,962,704 | * | 10/1999 | Inaba et al. ......................... | 549/341 |

FOREIGN PATENT DOCUMENTS

| | | |
|---|---|---|
| 43 33 686 | 4/1995 | (DE) . |
| WO95/09843 | 4/1995 | (WO) . |
| WO97/11937 | 4/1997 | (WO) . |
| WO97/11938 | 4/1997 | (WO) . |

OTHER PUBLICATIONS

Chemical abstract vol. 119 No. 225810, Shionogi, "Preparation of CIS–3–Alkoxy–4–Amino Pyrrolidine Derivatives" 1993.*

Bair et al.; "(1–Pyrenylmethyl) Amino Alcohols, A New Class of Antitumor DNA of Medicinal Intercalators. Discovery and Initial Amine Side Chain Structure–Activity Studies"; Journal Chemistry; vol. 33, No. 9; Sep. 1990; pp. 2385–2393; XP002099784.

Database WPI Week 9720; Derwent Publications Ltd.; AN 97225863; XP002099785 & WO 97 11938; Sep. 24, 1996.

* cited by examiner

*Primary Examiner*—John Kight
*Assistant Examiner*—Raymond Covington
(74) *Attorney, Agent, or Firm*—Foley & Lardner

(57) ABSTRACT

A method for producing an optically active amino alcohol compound of the formula [3], an enantiomer thereof or a salt thereof, comprising reacting a mesoepoxide compound of the formula [1] with a compound of the formula [2] in the presence of a mixed catalyst comprising a Lewis acid and a proton donor:

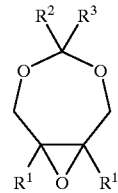

[1]

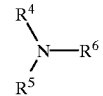

[2]

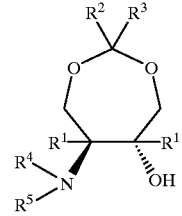

[3]

wherein $R^1$, $R^2$ and $R^3$ are each H, an optionally substituted lower alky, and the like, or $R^1$ and $R^1$ or $R^2$ and $R^3$ may form an optionally substituted ring; and $R^4$ and $R^5$ are each H, an optionally substituted lower alkyl, and the like, or $R^4$ and $R^5$ may form an optionally substituted ring together with the adjacent N, or an imide group or azide group together with the adjacent N, and $R^6$ is H or a silyl group. The present invention enables stereoselective production of a desired intermediate compound, which is an HIV protease inhibitor, extremely efficiently as compared to conventional methods. The method of the present invention is a very useful method which can be used not only for the production of said intermediate compound but also for the production of various other compounds.

12 Claims, No Drawings

PRODUCTION METHOD OF OPTICALLY ACTIVE AMINO ALCOHOLS

TECHNICAL FIELD OF THE INVENTION

The present invention relates to a method for producing an intermediate for the production of the compound of the formula [XVI]

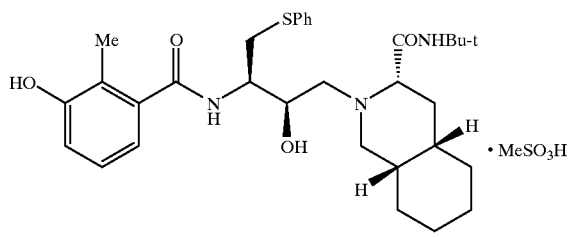

[XVI]

wherein Me is methyl, Bu-t is t-butyl and Ph is phenyl, which has a virus-derived protease inhibitory activity and which is a useful therapeutic agent for HIV infectious diseases.

BACKGROUND OF THE INVENTION

The above-mentioned compound [XVI] useful as an HIV protease inhibitor has been known from WO95/09843, and the production methods thereof have been known from WO97/11937 and WO97/11938.

However, these production methods cannot impart stereoselectivity to intermediates, and thus, they are not satisfactory in view of low yields of the objective intermediates. In addition, these methods require heating to 80–90° C. during reaction, as well as purification due to crystallization, since the resulting intermediate compound is a 1:1 mixture of isomers.

SUMMARY OF THE INVENTION

The present invention aims at solving the above-mentioned problems, and producing an optically active amino alcohol compound, an enantiomer thereof and a salt thereof stereoselectively at high yields as a highly pure salt.

The present inventors have conducted intensive studies in an attempt to solve the above-mentioned problems, and found that a ring opening of a mesoepoxide compound, using chiral or achiral amine and a mixed catalyst of a proton donor and a Lewis acid under mild temperature conditions leads to stereoselective production of an optically active amino alcohol compound, an enantiomer thereof and a salt thereof at high yields. In addition, they have found that the use of a chiral proton donor enables production of an amino alcohol at sufficient asymmetric yields by ring opening of an epoxy compound using achiral amine. They have also found that an important intermediate compound [5] and an enantiomer thereof to be mentioned later can be produced stereoselectively and highly efficiently in large amounts as crystalline salts having high purity by isomerizing the 7-membered moiety of said amino alcohol to a 5-membered structure and then removing the substituent(s) $R^4$ and/or $R^5$ on the nitrogen atom, which resulted in the completion of the present invention.

Accordingly, the present invention provides the following (1) to (10).
(1) A method for producing an optically active amino alcohol compound of the formula [3]

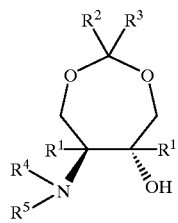

[3]

wherein
$R^1$, $R^2$ and $R^3$ are the same or different and each is a hydrogen atom, an optionally substituted lower alkyl, an optionally substituted aryl or an optionally substituted aralkyl, or $R^1$ and $R^1$ or $R^2$ and $R^3$ in combination may form an optionally substituted ring; and
$R^4$ and $R^5$ are the same or different and each is a hydrogen atom, an optionally substituted lower alkyl, an optionally substituted aryl, an optionally substituted aralkyl or an acyl, or $R^4$ and $R^5$ in combination may form an optionally substituted ring together with the adjacent nitrogen atom, or $R^4$ and $R^5$ in combination may form an imide group or an azide group together with the adjacent nitrogen atom,
an enantiomer thereof or a salt thereof, comprising reacting a mesoepoxide compound of the formula [1]

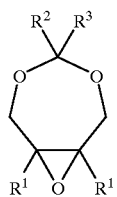

[1]

wherein $R^1$, $R^2$ and $R^3$ are as defined above, with a compound of the formula [2]

[2]

wherein $R^4$ and $R^5$ are as defined above, and $R^6$ is a hydrogen atom or a silyl group, in the presence of a mixed catalyst comprising a Lewis acid and a proton donor.
(2) The method according to (1) above, for producing an optically active amino alcohol compound of the formula [3']

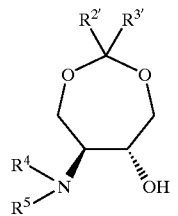

[3']

wherein
$R^{2'}$ and $R^{3'}$ are the same or different and each is a hydrogen atom, an optionally substituted lower alkyl or an aryl, or $R^{2'}$ and $R^{3'}$ in combination may form a cycloalkyl ring together with the adjacent carbon atom; and $R^4$ and $R^5$ are the same or different and each is a hydrogen atom, an optionally substituted lower alkyl, an optionally substituted aryl, an optionally substituted aralkyl or an acyl, or $R^4$ and $R^5$ in combination may form an optionally substituted ring together with the adjacent nitrogen atom, or $R^4$ and $R^5$ in combination may form an imide group or an azide group together with the adjacent nitrogen atom, an enantiomer thereof or a salt thereof, comprising reacting a mesoepoxide compound of the formula [1']

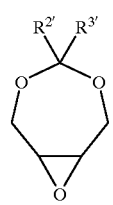

[1']

wherein $R^{2'}$ and $R^{3'}$ are as defined above, with a compound of the formula [2]

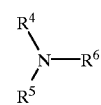

[2]

wherein $R^4$ and $R^5$ are as defined above and $R^6$ is a hydrogen atom or a silyl group, in the presence of a mixed catalyst comprising a Lewis acid and a proton donor.

(3) A method for producing an optically active 1,3-dioxolane compound of the formula [4]

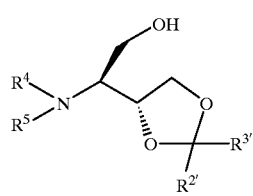

[4]

wherein $R^{2'}$ and $R^{3'}$ are the same or different and each is a hydrogen atom, an optionally substituted lower alkyl or an aryl, or $R^{2'}$ and $R^{3'}$ in combination may form a cycloalkyl ring together with the adjacent carbon atom; and $R^4$ and $R^5$ are the same or different and each is a hydrogen atom, an optionally substituted lower alkyl, an optionally substituted aryl, an optionally substituted aralkyl or an acyl, or $R^4$ and $R^5$ in combination may form an optionally substituted ring together with the adjacent nitrogen atom, or $R^4$ and $R^5$ in combination may form an imide group or an azide group together with the adjacent nitrogen atom, or an enantiomer thereof, comprising reacting a mesoepoxide compound of the formula [1']

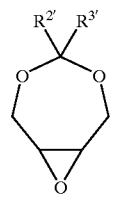

[1']

wherein $R^{2'}$ and $R^{3'}$ are as defined above, with a compound of the formula [2]

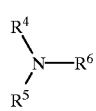

[2]

wherein $R^4$ and $R^5$ are as defined above and $R^6$ is a hydrogen atom or a silyl group, in the presence of a mixed catalyst comprising a Lewis acid and a proton donor, to give an optically active amino alcohol compound of the formula [3']

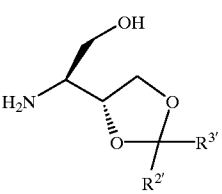

[3']

wherein $R^{2'}$, $R^{3'}$, $R^4$ and $R^5$ are as defined above, an enantiomer thereof or a salt thereof, and isomerizing the resulting compound to a 5-membered ring in the presence of an acid.

(4) A method for producing an optically active amino alcohol compound having 1,3-dioxolane, which is represented by the formula [5]

[5]

wherein $R^{2'}$ and $R^{3'}$ are the same or different and each is a hydrogen atom, an optionally substituted lower alkyl or an aryl, or $R^{2'}$ and $R^{3'}$ in combination may form a cycloalkyl ring together with the adjacent carbon atom, an enantiomer thereof or a salt thereof, comprising reacting a mesoepoxide compound of the formula [1']

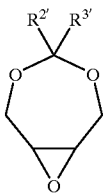

[1']

wherein $R^{2'}$ and $R^{3'}$ are as defined above, with a compound of the formula [2]

[2]

wherein $R^4$ and $R^5$ are the same or different and each is a hydrogen atom, an optionally substituted lower alkyl, an optionally substituted aryl, an optionally substituted aralkyl or an acyl, or $R^4$ and $R^5$ in combination may form an optionally substituted ring together with the adjacent nitrogen atom, or $R^4$ and $R^5$ in combination may form an imide group or an azide group together with the adjacent nitrogen atom; and $R^6$ is a hydrogen atom or a silyl group, in the presence of a mixed catalyst comprising a Lewis acid and a proton donor, to give an optically active amino alcohol compound of the formula [3']

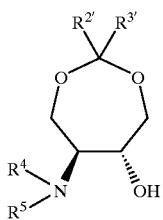

[3']

wherein $R^{2'}$, $R^{3'}$, $R^4$ and $R^5$ are as defined above, an enantiomer thereof or a salt thereof; converting the resulting compound to an optically active 1,3-dioxolane compound of the formula [3]

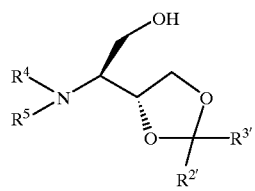

[4]

wherein $R^{2'}$, $R^{3'}$, $R^4$ and $R^5$ are as defined above, or an enantiomer thereof, in the presence of an acid, and eliminating the substituent(s) $R^4$ and/or $R^5$ on the nitrogen atom.

(5) The production method of (1) or (2) above, wherein the proton donor is at least one member selected from the group consisting of (R)-1,1-bi-2-naphthol, (S)-1,1'-bi-2-naphthol, catechol and 4-tert-butylcatechol, and the Lewis acid is at least one member selected from the group consisting of titanium tetraisopropoxide, titanium tetrachloride, tin chloride, copper chloride, iron chloride, zinc chloride, zinc bromide, zinc iodide, aluminum chloride, aluminum bromide, alkylaluminum, alkylaluminum chloride, aluminum alkoxide, magnesium chloride, zirconocene, zirconium tetrapropoxide, zirconium chloride, zirconium sulfate, zirconium fluoride, boron bromide, boron chloride and boron fluoride.

(6) The production method of the above (3), wherein the proton donor is at least one member selected from the group consisting of (R)-1,1'-bi-2-naphthol, (S)-1,1'-bi-2-naphthol, catechol and 4-tert-butylcatechol, and the Lewis acid is at least one member selected from the group consisting of titanium tetraisopropoxide, titanium tetrachloride, tin chloride, copper chloride, iron chloride, zinc chloride, zinc bromide, zinc iodide, aluminum chloride, aluminum bromide, alkylaluminum, alkylaluminum chloride, aluminum alkoxde, magnesium chloride, zirconocene, zirconium tetrapropoxide, zirconium chloride, zirconium sulfate, zirconium fluoride, boron bromide, boron chloride and boron fluoride.

(7) The production method of the above (4), wherein the proton donor is at least one member selected from the group consisting of (R)-1,1'-bi-2-naphthol, (S)-1,1'-bi-2-naphthol, catechol and 4-tert-butylcatechol, and the Lewis acid is at least one member selected from the group consisting of titanium tetraisopropoxide, titanium tetrachloride, tin chloride, copper chloride, iron chloride, zinc chloride, zinc bromide, zinc iodide, aluminum chloride, aluminum bromide, alklaluminum, alkylaluminum chloride, aluminum alkoxde, magnesium chloride, zirconocene, zirconium tetrapropoxide, zirconium chloride, zirconium sulfate, zirconium fluoride, boron bromide, boron chloride and boron fluoride.

(8) The production method of (1) or (2) above, wherein the proton donor is (R)-1,1'-bi-2-naphthol or (S)-1,1'-bi-2-naphthol, and the Lewis acid is titanium tetraisopropoxide.

(9) The production method of the above (3), wherein the proton donor is (R)-1,1'-bi-2-naphthol or (S)-1,1'-bi-2-naphthol, and the Lewis acid is titanium tetraisopropoxide.

(10) The production method of the above (4), wherein the proton donor is (R)-1,1'-bi-2-naphthol or (S)-1,1'-bi-2-naphthol, and the Lewis acid is titanium tetraisopropoxide.

DETAILED DESCRIPTION OF THE INVENTION

In the present specification, each group means the following.

The lower alkyl means, for example, alkyl having 1 to 6 carbon atoms and may be linear or branched. Examples thereof include methyl, ethyl, propyl, isopropyl, butyl, isobutyl, sec-butyl, tert-butyl, pentyl, isopentyl, neopentyl, tert-pentyl, hexyl, isohexyl and neohexyl, with preference given to lower alkyl having 1 to 4 carbon atoms such as methyl, ethyl, propyl, isopropyl, butyl, isobutyl, sec-butyl and tert-butyl.

The optionally substituted lower alkyl includes the abovementioned lower alkyl which may be substituted by one or more substituents which do not influence the reaction. Examples of the substituents include halogen atoms such as chlorine, bromine, fluorine, iodine and the like; hydroxy; amino; nitro; alkylamino such as primary alkylamino having 1 to 6 carbon atoms (e.g., methylamino, ethylamino and the like), secondary alkylamino having 2 to 6 carbon atoms (e.g., dimethylamino, diethylamino and the like); cyano; cycloalkyl having 3 to 7 carbon atoms such as cyclopropyl, cyclobutyl, cyclohexyl and the like; lower alkoxy having 1 to 6 carbon atoms such as methoxy, ethoxy and the like; acyloxy such as acetoxy, benzoyloxy and the like; aralkyloxy such as benzyloxy and the like; lower alkoxycarbonyl having 2 to 6 carbon atoms such as methoxycarbonyl, ethoxycarbonyl and the like; and the like. Preferred are hydroxy, halogen atom, amino, nitro, aralkyloxy, lower alkoxy having 1 to 6 carbon atoms and acyloxy, with particular preference given to hydroxy, acyloxy, halogen atom and lower alkoxy having 1 to 6 carbon atoms. The position and number of substituents on lower alkyl are not particularly limited. However, preferred is a 1–3 substituted compound, particularly, a 1–2 substituted compound.

Examples of the optionally substituted lower alkyl at $R^2$, $R^3$, $R^{2'}$ and $R^{3'}$ include methyl, ethyl, propyl, isopropyl, butyl, isobutyl, sec-butyl, tert-butyl, pentyl, isopentyl, neopentyl, tert-pentyl and the like, with preference given to methyl, ethyl, propyl, isopropyl, butyl, isobutyl, sec-butyl and tert-butyl, and more preference given to methyl.

Examples of aryl include phenyl, naphthyl, biphenyl and the like, with preference given to phenyl.

The optionally substituted aryl includes the above-mentioned aryl which may be substituted by one or more substituents having no influence on the reaction. Examples of the substituent include lower alkyl having 1 to 6 carbon atoms such as methyl, ethyl, propyl and the like; hydroxy; halogen atoms such as chlorine, bromine, fluorine, iodine and the like; amino; nitro; alkylamino such as primary alkylamino having 1 to 6 carbon atoms (e.g., ethylamino and the like) and secondary alkylamino having 2 to 6 carbon atoms (e.g., dimethylamino and the like); cyano; cycloalkyl having 3 to 7 carbon atoms such as cyclohexyl and the like; lower alkoxy having 1 to 6 carbon atoms such as methoxy, ethoxy and the like; acyloxy such as alkanoyloxy having 2 to 6 carbon atoms (e.g., acetyloxy, propionyloxy and the like); lower alkoxycarbonyl having 2 to 6 carbon atoms such as methoxycarbonyl and the like; and the like. Preferred are lower alkyl having 1 to 6 carbon atoms, hydroxy, halogen atom, amino, nitro, lower alkoxy having 1 to 6 carbon atoms and acyloxy having 1 to 6 carbon atoms, and particularly preferred are lower alkyl having 1 to 6 carbon atoms, hydroxy, acyloxy having 1 to 6 carbon atoms, halogen atom and lower alkoxy having 1 to 6 carbon atoms. The position and number of substituents on aryl are not particularly limited. However, preferred is a 1–3 substituted compound, particularly, a 1–2 substituted compound.

The aralkyl has phenyl at its aryl moiety and, for example, alkyl having 1 to 6 carbon atoms as its alkyl moiety. Specific examples are benzyl, phenethyl, phenylpropyl, phenylbutyl, phenylhexyl and the like, with preference given to benzyl.

The optionally substituted aralkyl is that wherein hydrogen in the alkyl moiety and/or hydrogen on the aryl ring of the above-mentioned aralkyl may be substituted by one or more substituents having no influence on the reaction. The alkyl moiety is preferably on the carbon adjacent to the aromatic ring. Specific examples of the alkyl moiety include lower alkyl having 1 to 6 carbon atoms such as methyl, ethyl, propyl and the like; cycloalkyl having 3 to 7 carbon atoms such as cyclohexyl and the like; and the like, with preference given to lower alkyl having 1 to 6 carbon atoms. Examples of the substituent on the aryl ring include lower alkyl having 1 to 6 carbon atoms such as methyl, ethyl, propyl and the like; hydroxy; halogen atoms such as chlorine, bromine, fluorine, iodine and the like; amino; nitro; alkylamino such as primary alkylamino having 1 to 6 carbon atoms (e.g., ethylamino and the like) and secondary alkylamino having 2 to 6 carbon atoms (e.g., dimethylamino and the like); cyano; cycloalkyl having 3 to 7 carbon atoms such as cyclohexyl and the like; lower alkoxy having 1 to 6 carbon atoms such as methoxy, ethoxy, propoxy and the like; acyloxy such as acetyloxy, propionyloxy and the like; alkoxycarbonyl having 2 to 6 carbon atoms such as methoxycarbonyl and the like; and the like. Preferred are lower alkyl having 1 to 6 carbon atoms, hydroxy, halogen atom, amino, nitro, lower alkoxy having 1 to 6 carbon atoms, acyloxy and the like, and particularly preferred are lower alkyl having 1 to 6 carbon atoms, hydroxy, acyloxy, halogen atom and lower alkoxy having 1 to 6 carbon atoms. The position and number of substituents on the aryl ring and in the alkyl moiety are not particularly limited. However, preferred is a 1–3 substituted compound, particularly, a 1–2 substituted compound.

The optionally substituted aralkyl at $R^4$ and $R^5$ is exemplified by benzyl, 1-phenylethyl, diphenylnethyl, 2,2-diphenylethyl, trityl, fluorenyl, dibenzosuberanyl and the like, with preference given to benzyl and 1-phenylethyl.

Examples of acyl include acetyl, propionyl, butyryl, pivaloyl, benzoyl and the like, with preference given to benzoyl.

A silyl group is exemplified by trimethylsilyl, t-butyldimethylsilyl, t-butyldiphenylsilyl and the like, with preference given to trimethylsilyl.

The ring of the optionally substituted ring in "$R^1$ and $R^1$ in combination may form an optionally substituted ring" specifically means cyclopropane, cyclobutane, cyclopentane, cyclohexane, cyclohexene and the like having meso structure, preferably cyclohexane and cyclopentane. These rings may have optional substituents as long as the meso structure can be maintained. Such substituent is exemplified by those shown above with respect to "optionally substituted aryl", which is preferably lower alkyl having 1 to 6 carbon atoms, particularly preferably methyl. The position and number of substituents are not particularly limited. However, preferred is a 1–3 substituted compound, particularly, a 1–2 substituted compound. Examples of the "optionally substituted ring" include 4,4-dimethylcyclopentane.

The ring of the optionally substituted ring in the "$R^2$ and $R^3$ in combination may form an optionally substituted ring" is a cycloalkyl ring, which is, for example, cycloalkyl ring having 3 to 7 carbon atoms. Specific examples thereof include cyclopropyl ring, cyclobutyl ring, cyclopentyl ring, cyclohexyl ring, cycloheptyl ring, cyclooctyl ring, perhydronaphthyl ring and the like. Preferred are cycloalkyl ring having 3 to 6 carbon atoms, such as cyclopropyl ring, cyclobutyl ring, cyclopentyl ring, cyclohexyl ring and the like. Such substituent is exemplified by those shown above with respect to "optionally substituted aryl" and other substituents. Preferred is lower alkyl having 1 to 6 carbon atoms, particularly preferably methyl. The position and number of substituents are not particularly limited. However, preferred is a 1–3 substituted compound, particularly, a 1–2 substituted compound.

The ring of the optionally substituted ring in the "$R^4$ and $R^5$ in combination may form an optionally substituted ring together with the adjacent nitrogen atom" is, for example, pyrrolidine, piperidine, morpholine, 2,5-diphenylpyrrolidine, 2,6-diphenylpiperidine and the like. Preferred is 2,5-diphenylpyrrolidine.

The imide group of the "$R^4$ and $R^5$ in combination may form an imide group together with the adjacent nitrogen atom" may be, for example, succinimide, maleimide, phthalimide and the like, with preference given to phthalmide.

The azide group of the "$R^4$ and $R^5$ may form an azide group together with the adjacent nitrogen atom" may be, for example, trialkylsilyl azide and the like, which is specifically trimethylsilyl azide, t-butyl dimethylsilyl azide and the like, with preference given to trimethylsilyl azide.

The cycloalkyl ring of the "$R^{2'}$ and $R^{3'}$ in combination may form a cycloalkyl ring together with the adjacent carbon atom" is, for example, cycloalkyl ring having 3 to 10 carbon atoms, which is exemplified by cyclopropyl ring, cyclobutyl ring, cyclopentyl ring, cyclohexyl ring, cycloheptyl ring, cyclooctyl ring, perhydronaphthyl ring and the like, with preference given to a cycloalxyl ring having 3 to 6 carbon atoms such as cyclopropyl ring, cyclobutyl ring, cyclopentyl ring, cyclohexyl ring and the like.

Examples of the "proton donor" include catechols such as catechol, 3,5-di-tert-butylcatechol, 3-methylcatechol, 4-nitrocatechol, 4-tert-butylcatechol and the like; phenols such as (R)-1,1'-bi-2-naphthol, (S)-1,1'-bi-2-naphthol, phenol, 2,2'-biphenol and the like; organic acids such as acetic acid, formic acid, propionic acid, oxalic acid, malonic acid and the like; alcohols such as diisopropyl tartrate, diethyl tartrate, (+)-trans-α,α'-(2,2-dimethyl-1,3-dioxolane-4,5-diyl)bis-(diphenylnethanol), (−)-trans-α,α'-(2,2-dimethyl-1,3-dioxolane-4,5-diyl)bis(diphenylmethanol) and the like; and the like. These proton donors may be used alone or in combination. Preferred proton donor is phenol, particularly (R)-1,1'-bi-2-naphthol and (S)-1,1'-bi-2-naphthol.

Examples of the Lewis acid include titanium tetrachloride, tin chloride, copper chloride, iron chloride, zinc chloride, zinc bromide, zinc iodide, magnesium chloride, titanium alkoxide (e.g., titanium methoxide, titanium ethoxide, titanium tetraisopropoxide and the like), cerium chloride, samarium iodide, samarium chloride, europium chloride, ytterbium chloride, boron bromide, boron chloride, boron fluoride, aluminum chloride, aluminum bromide, alklaluminum (e.g., trimethylaluminum, triethylaluminum, tributylaluminum and the like), alkylaluminum chloride (e.g., diethylaluminum chloride, ethylaluminum dichloride and the like), aluminum alkoxide (e.g., aluminum methoxide, aluminum ethoxide, aluminum isopropoxide and the like), zirconocene, zirconium tetrapropoxide, zirconium chloride, zirconium sulfate, zirconium fluoride and the like, with preference given to titanium alkoxide, and more preference given to titanium tetraisopropoxide. These Lewis acids may be used alone or in combination.

While the salt is not particularly limited as to its kind, it may be a pharmaceutically acceptable salt such as inorganic acid salts (e.g., hydrochloride, hydrobromide, sulfate, phosphate and the like); organic acid salts (e.g., formate, acetate, benzoate, trifluoroacetate, maleate, tartrate and the like); sulfonates (e.g., methanesulfonate, benzenesulfonate, p-toluenesulfonate and the like); amino acid salts (e.g., arginine, aspartate, glutamate and the like); and the like.

The methods for producing the compounds of the formulas [3']and [5], which are important intermediates of the present invention, are shown in detail in the following.

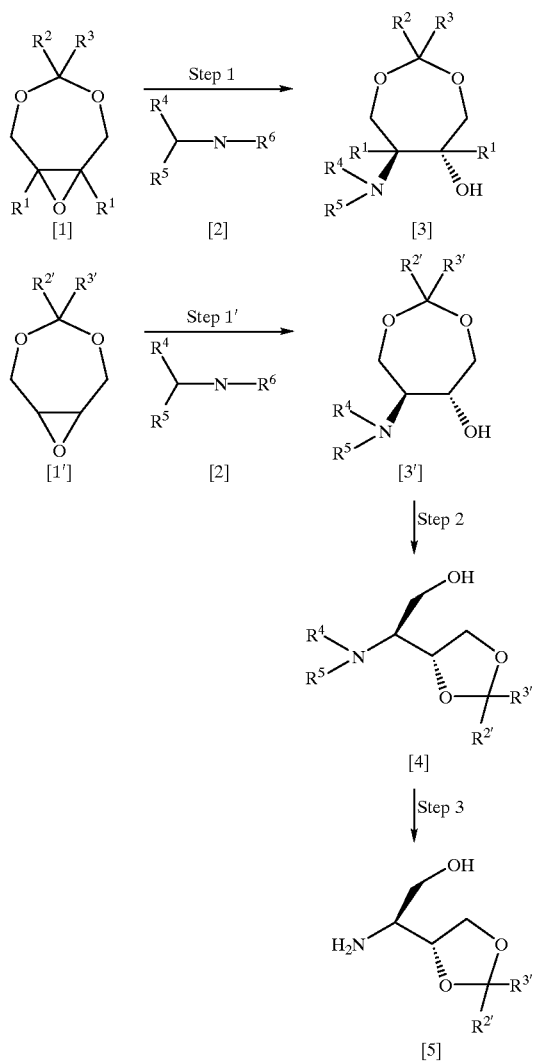

wherein $R^1$, $R^2$, $R^3$, $R^{2'}$, $R^{3'}$, $R^4$, $R^5$ and $R^6$ are as defined above.
<General production method>
Step 1 and Step 1' (Epoxy ring opening by amine)

The compounds [1] or [1'] obtained by known methods are subjected to epoxy ring opening with a compound of the formula [2] in a suitable solvent in the presence of a mixed catalyst comprising a Lewis acid and a proton donor, whereby optically active compounds [3] or [3'] or enantiomers thereof are obtained. Either or both of the compound [2] and proton donor here is/are chiral compound(s).

The compound of the formula [2] may be, for example, benzylamines such as aralkylamine [e.g., benzylamine, diphenylmethylamine, 1,1-diphenylethylainine, 1-methyl-1-phenethylamine, (R)-1-phenethylamine, (S)-1-phenethylamine, (R)-1-(1-naphthyl)ethylamine, (S)-1-(1-naphthyl)ethylamine, (R)-phenylglycinol, (S)-phenylglycinol, tritylainine, fluorenylamine, dibenzosuberanylamine and the like], alkylamine (e.g., methylamine, ethylamine, propylamine, tert-butylamine and the like), amino acid derivative [e.g., (R)-phenyl glycinemethyl ester, (S)-phenyl glycinemethyl ester, (R)-serine methyl ester, (S)-serine methyl ester and the like], aromatic amine (e.g., aniline, 1-naphthylamine, 2-naphthylamine and the like), secondary amine (e.g., dibenzylamine, morpholine, piperidine, pyrrolidine and the like), imides (e.g., succinimide, maleimide, phthalimide, and the like); silylazide (e.g., trimethylsilyl azide, t-butyldimethylsilyl azide and the like); and the like, with preference given to benzylamines, and more preference given to (R)-1-phenethylamine and (S)-1-phenethylamine.

Suitable solvent to be used in the reaction includes, for example, alcohol solvents such as methanol, ethanol, n-propyl alcohol, isopropyl alcohol, n-butyl alcohol and tert-butyl alcohol; hydrocarbon solvents such as benzene, toluene, hexane, xylene, pentane, hexapentane, cyclohexane, heptane and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; polar solvents such as N,N-dimethylformamide, dimethyl sulfoxide, acetonitrile, acetone, water and the like; and the like, which may be used alone or in combination. Preferred are hydrocarbon solvents and water. More preferred are toluene, heptane, water and mixed solvents thereof.

Examples of the proton donor include catechols (e.g., catechol, 3,5-di-tert-butylcatechol, 3-methylcatechol, 4-nitrocatechol, 4-tert-butylcatechol and the like), phenols [e.g., (R)-1,1'-bi-2-naphthol, (S)-1,1'-bi-2-naphthol, phenol, 2,2'-biphenol and the like], organic acids (e.g., acetic acid, formic acid, propionic acid, oxalic acid, malonic acid and the like), alcohols [e.g., diisopropyl tartrate, diethyl tartrate, (+)-trans-α,α'-(2,2-dimethyl-1,3-dioxolane-4,5-diyl)bis(diphenylmethanol), (−)-trans-α,α'-(2,2-dimethyl-1,3-dioxolane-4,5-diyl)bis(diphenylmethanol) and the like], and the like, with preference given to phenols, and more preference given to (R)-1,1'-bi-2-naphthol and (S)-1,1'-bi-2-naphthol.

Examples of the Lewis acid include titanium tetrachloride, tin chloride, copper chloride, iron chloride, zinc chloride, zinc bromide, zinc iodide, magnesium chloride, titanium alkoxide (e.g., titanium methoxide, titanium ethoxide, titanium tetraisopropoxide and the like), cerium chloride, samarium iodide, samarium chloride, europium chloride, ytterbium chloride, boron bromide, boron chloride, boron fluoride, aluminum chloride, aluminum bromide, alkylaluminum (e.g., trimethylaluminum, triethylaluminum, tributylaluminum and the like), alkylaluminum chloride (e.g., diethylaluminum chloride, ethylaluminum dichloride and the like), aluminum alkoxide (e.g., aluminum methoxide, aluminum ethoxide, aluminum isopropoxide and the like), zirconocene, zirconium tetrapropoxide, zirconium chloride, zirconium sulfate, zirconium fluoride and the like, with preference given to titanium alkoxde, and more preference given to titanium tetraisopropoxde.

Examples of the mixed catalyst comprising a Lewis acid and a proton donor include a combination of optically active 1,1'-bi-2-naphthol and titanium tetraisopropoxide.

The reaction temperature is 0–100° C., preferably 20–50° C., and the reaction time is about 10–50 hours, preferably about 15–24 hours.

Step 2 (Isomerization from 7-membered ring to 5-membered ring)

In this step, chiral compound [4] or an enantiomer thereof is obtained by isomerizing the 7-membered ring of compound [3'] or an enantiomer thereof to a more thermodynamically stable 5-membered ring in a suitable solvent and in the presence of an acid.

Suitable solvent to be used in the reaction includes, for example, hydrocarbon solvents such as benzene, toluene, hexane, xylene and the like; ether solvents such as diethyl ether, 1,2-dimethoxyethane, tetrahydrofuran, diglyme, 2,2-dimethoxypropane and the like; halogen solvents such as dichloromethane, chloroform, carbon tetrachloride, 1,2-dichloroethane and the like; ester solvents such as ethyl acetate, methyl acetate, butyl acetate and the like; polar solvents such as N,N-dimethylformamide, dimethyl sulfoxide, acetonitrile, acetone and the like; mixed solvents thereof; and the like, with preference given to acetone.

The acid is exemplified by inorganic acids (e.g., sulfuric acid, hydrochloric acid, nitric acid and the like); organic acids (e.g., acetic acid, trifluoroacetic acid, methanesulfonic acid, p-toluenesulfonic acid, p-toluenesulfonic pyridinium, benzenesulfonic acid, camphorsulfonic acid and the like); and the like, with preference given to organic acid, and more preference given to methanesulfonic acid.

The reaction temperature is suitably 0–100° C., preferably 20–50° C., and the reaction time is preferably 1–5 hours.

Step 3 (Elimination of amino-protecting group)

In this step, the substituent $R^4$ and/or $R^5$ on the nitrogen atom of compound [4] obtained in Step 2 are/is removed under suitable conditions to give chiral compound [5] or an enantiomer thereof and then a salt thereof.

The conditions for the elimination of the substituent are appropriately determined according to the kind of substituent on the nitrogen atom. For example, when $R^4$ is 1-phenethyl and $R^5$ is hydrogen, the substituent on the nitrogen atom can be removed by catalytic reduction in a suitable solvent in the presence of a suitable catalyst and a hydrogen source. A suitable acid may be added to accelerate the reaction and to give the product as a salt.

Examples of the suitable catalyst include palladium catalyst, platinum catalyst, rhodium catalyst, ruthenium catalyst and the like, with preference given to palladium catalyst, and more preference given to palladium carbon.

The hydrogen source may be, for example, hydrogen gas, ammonium formate, formic acid, cyclohexadiene and the like, with preference given to hydrogen gas.

Suitable solvent includes, for example, alcohol solvents such as methanol, ethanol, n-propyl alcohol, isopropyl alcohol, n-butyl alcohol, t-butyl alcohol and the like; hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as N,N-dimethylformamide, formic acid, acetic acid, water and the like; mixed solvents thereof; and the like; with preference given to alcohol solvents and more preference given to isopropyl alcohol.

Suitable acid is exemplified by inorganic acids such as hydrochloric acid, hydrobromic acid, sulfuric acid, phosphoric acid and the like; organic acids such as formic acid, acetic acid, benzoic acid, trifluoroacetic acid, maleic acid, tartaric acid and the like; sulfonic acids such as methanesulfonic acid, benzenesulfonic acid, p-toluenesulfonic acid and the like, amino acids such as arginine, asparagine, glutamic acid and the like, with preference given to organic acids and more preference given to benzoic acid.

The reaction temperature is 0–100° C., preferably 20–60° C., and the reaction time is 5–15 hours.

The present invention is described in more detail by way of Examples, to which the present invention is not limited.

The flow chart of the reactions in the Examples is given below.

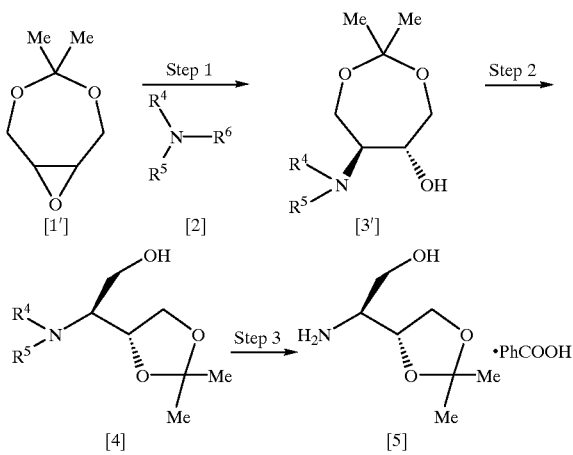

wherein Ph is phenyl, Me is methyl and $R^4$, $R^5$ and $R^6$ are as defined above.

EXAMPLE 1
(Production of compound [3']—Step 1')

Heptane-toluene (9:1, volume ratio, 350 ml) was added to (S)-1,1'-bi-2-naphthol (1.89 g), and titanium tetraisopropoxide (Ti(OPr$^i$)$_4$, 1.95 ml) was added under a nitrogen atmosphere, which was followed by stirring for 10 min at room temperature. (R)-1-Phenethylamine (compound [2], 85 ml), water (0.5 ml) and 4,4-dimethyl-3,5,8-trioxabicyclo[5.1.0]octane (compound [1'], 100 g) obtained by a known method were successively added with stirring, and the mixture was stirred at 40° C. for 24 hr. Toluene was added to the reaction mixture and the mixture was stirred at 40° C. for 1 hr. Then, the mixture was cooled to 10° C. or less over one hour and stirred for one more hour. The crystals in the reaction mixture were collected by filtration and washed with heptane-toluene (2:1, volume ratio) to give (5R,6S)-2,2-dimethyl-6-[(R)-1-phenethylamino]-1,3-dioxepan-5-ol (compound [3'], 159 g, yield 91%) as yellow crystals. mp. 108–109° C.

$^1$H-NMR(CDCl$_3$,300 MHz): δ 7.33–7.22 (m,5H) ,3.95 (q,1H,J=6.5 Hz), 3.75 (dd,1H,J=1.8,12.1 Hz), 3.74 (dd,1H, J=2.0,12.5 Hz), 3.52 (dd,1H,J=5.5, 12.5 Hz), 3.48 (ddd,1H, J=0.5,5.9,12.1 Hz), 3.37 (dt,1H,J=1.4,5.6 Hz), 2.44 (brs, 1H), 2.34 (dt,1H,J=1.7,5.5 Hz), 1.34 (d,3H,J=6.5 Hz), 1.34 (s,3H), 1.31 (s,3H).

IR(KBr) 3406,2590,1452,1374,1219,1072,1052,841,758, 696 cm$^{-1}$, [α]D25+91.0° (c1.00, MeOH); Anal. Calcd for C$_{15}$H$_{23}$NO$_3$: C,67.90; H,8.74; N,5.28; Found C,67.90; H,9.01; N,5.31.

EXAMPLE 2

Toluene (60 ml) was added to (S)-1,1'-bi-2-naphthol (426 mg), and titanium tetraisopropoxide (Ti(OPr$^i$)$_4$, 439 μl) was added under a nitrogen atmosphere. The mixture was stirred for 10 min at room temperature. Benzylamine (21.6 ml), water (225 μl) and 4,4-dimethyl-3,5,8-trioxabicyclo-[5.1.0]octane (compound [1'], 30 g) obtained by a known method were successively added with stirring, and the mixture was stirred at 40° C. for 24 hr. 1N NaOH (30 ml) was added to the reaction mixture and the mixture was refluxed at 90° C. for 1 hr. The aqueous layer was removed at 50° C. and active charcoal (0.9 g) was added to the obtained organic layer, and the mixture was azeotropically concentrated under atmospheric pressure. The active charcoal was filtered off and the filtrate was concentrated under reduced pressure to give crude (5R,6S)-2,2-dimethyl-6-benzylamino-1,3-dioxepan-5-ol (50 g, 88% ee) as a yellow oil, which was used in the next step without purification. The analytically pure sample was obtained by column chromatography.

$^1$H-NMR(CDCl$_3$,300 MHz): δ 7.33–7.23 (m,5H), 3.92 (d,1H,J=13.2 Hz), 3.78 (d,1H,J=13.2 Hz), 3.80–3.76 (m,2H), 3.59–3.49 (m,3H), 2.56 (m,1H), 2.04 (brs,1H), 1.33 (s,3H), 1.32 (s,3H).

IR(CHCl$_3$) 3416,2941,1454,1372,1219,1159,1047,842, 739,699 cm$^{-1}$; [α]D+50.6° (c0.5, MeOH); HRMS Calcd for C$_{14}$H$_{22}$O$_3$N (M$^+$+1): 252. 1594; Found: 252. 1591.

EXAMPLE 3

In the same manner as in Example 2, (S)-1,1'-bi-2-naphthol (19.9 mg), toluene (2 ml), titanium tetraisopropoxide (Ti(OPr$^i$)$_4$, 10 μl), diphenylmethylamine (1.2 ml), water (10 μl) and 4,4-dimethyl-3,5,8-trioxabicyclo[5.1.0]octane (compound [1'], 1.0 g) were treated and purified by column chromatography to give (5R,6S)-2,2-dimethyl-6-benzhydrilamino-1,3-dioxepan-5-ol (2.21 g, yield 97%, 90% ee) as a colorless wax.

$^1$H-NMR(CDCl$_3$,300 MHz): δ 7.44–7.17 (m,10H), 5.00 (s,1H), 4.02 (ddd,1H, J=3.0,14.4,17.1 Hz), 3.82 (d,1H,J= 11.4 Hz), 3.77 (dd,1H,J=1.8,13.2 Hz), 3.60–3.51 (m,3H), 2.54 (dt,1H,J=1.2,4.5), 1.82 (brs,1H), 1.32 (s,3H), 1.31 (s,3H).

IR(CHCl$_3$) 3345,2954,1450,1373,1218,1156,1050,848, 744,698 cm$^{-1}$; [α]D+42.8° (c0.5, MeOH); HRMS Calcd for C$_{20}$H$_{26}$O$_3$N (M$^+$+1): 328. 1906; Found: 328. 1906.

EXAMPLE 4

Heptane (2 ml) was added to 3,5-di-t-butylcatechol (617 mg), and titanium tetraisopropoxide (Ti(OPr$^i$)$_4$, 818 μl) was added under a nitrogen atmosphere. The mixture was stirred for 20 min at room temperature. (R)-1-phenethylamine (1.79 ml), water (20 μl) and 4,4-dimethyl-3,5,8-trioxabicyclo [5.1.0]octane (compound [1'], 2.0 g) obtained by a known method were successively added with stirring, and the mixture was stirred at room temperature for 20 hr. Heptane (4.6 ml) was added to the reaction mixture and the mixture was stirred under ice-cooling for 1 hr. The resulting crystals were collected by filtration to give (5R,6S)-2,2-dimethyl-6-[(R)-1-phenethylamino]-1,3-dioxepan-5-ol (compound [3'], 2.14 g, yield 57%).

EXAMPLE 5

In the same manner as in Example 2, (S)-1,1'-bi-2-naphthol (9.9 mg), heptane-toluene (9:1, volume ratio, 3.5 ml), titanium tetraisopropoxide (Ti(OPr$^i$)$_4$, 10.2 μl), (S)-1-phenethylamine (0.85 ml), water (20 μl) and 4,4-dimethyl-3,5,8-trioxabicyclo[5.1.0]octane (compound [1'], 1.0 g) were treated to give crude (5R,6S)-2,2-dimethyl-6-[(S)-1-phenethylamine]-1,3-dioxepan-5-ol (1.8 g, 97.6% de) as a yellow oil.

EXAMPLE 6

In the same manner as in Example 2, (S)-1,1 '-bi-2-naphthol (284 mg), heptane-toluene (9:1 (volume ratio), 105 ml), titanium tetraisopropoxide (Ti(OPr$^i$)$_4$, 293 μl), ()-1-phenethylamine (25.5 ml), water (300 μl) and 4,4-dimethyl-3,5,8-trioxabicyclo[5.1.0]octane (compound [1'], 30 g) were treated to give crude (5R,6S)-2,2-dimethyl-6-(1-phenethylamino)-1,3-dioxepan-5-ol (55 g, 1:1 diastereomer mixture) as a yellow oil, which was used in the next step without purification.

EXAMPLE 7

(Production of compound [4]—Step 2)

Acetone (200 ml) and 2,2-dimethoxypropane (4.63 ml) were added to (5R,6S)-2,2-dimethyl-6-[(R)-1-phenethylamino]-1,3-dioxepan-5-ol (100.0 g) obtained in Example 1, and the mixture was cooled in an ice bath under a nitrogen atmosphere. Methanesulfonic acid (29.3 ml) was added dropwise under stirring while retaining an inside temperature at not more than 25° C. The mixture was washed with acetone (1.0 ml), and the ice bath was removed, which was followed by stirring at room temperature. Three hours later, a potassium carbonate (62.5 g)/water (300 ml) solution was added, and the mixture was stirred for 15 min at room temperature. The reaction mixture was extracted with toluene. The organic layer was concentrated under reduced pressure to give crude (2S)-2-[(R)-1-phenethylamino]-2-[(4R)-2,2-dimethyl-1,3-dioxolan-4-yl]ethanol (compound [4], 107.4 g) as a colorless oil, which was used in the next step without purification.

$^1$H-NMR(CDCl$_3$,300 MHz): δ 7.34–7.20 (m,5H), 4.15 (q,1H,J=7.0 Hz), 3.97 (dd,1H,J=1.0,7.0 Hz), 3.87 (q,1H,J=7.0 Hz), 3.74–3.69 (m,2H), 3.48 (dd,1H,J=2.0,11.0 Hz), 2.45 (m,1H), 2.34 (brs,1H), 1.38 (d,3H, J=7.0 Hz), 1.33 (s,3H), 1.31 (s,3H).

EXAMPLE 8

In the same manner as in Example 7, crude (5R,6S)-2,2-dimethyl-6-benzylamino-1,3-dioxepan-5-ol (50 g, 88% ee) obtained in Example 2, acetone (100 ml), 2,2-dimethoxypropane (2.4 ml), methanesulfonic acid (15.4 ml) and a potassium carbonate (32.9 g)/water (150 ml) solution were treated to give crude (2S)-2-benzylamino-2-[(4R)-2,2-dimethyl-1,3-dioxolan-4-yl]ethanol (compound [4], 52 g) as a yellow oil, which was used in the next step without purification.

$^1$H-NMR(CDCl$_3$,300 MHz): δ 7.34–7.26 (m,5H), 4.20 (q,1H,J=6.6,13.3 Hz), 4.05 (t,1H,J=7.8 Hz), 3.90 (d,1H,J=13.3 Hz), 3.80–3.69 (m,3H), 3.36 (d,1H,J=11.3 Hz), 2.70 (brt,1H,J=3.6 Hz), 2.22 (brs,1H), 1.38 (s,3H), 1.34 (s,3H).

EXAMPLE 9

In the same manner as in Example 7, crude (5R,6S)-2,2-dimethyl-6-(1-phenethylamino)-1,3-dioxepan-5-ol (55 g, 1:1 diastereomer mixture) obtained in Example 6, acetone (100 ml), 2,2-dimethoxypropane (2.4 ml), methanesulfonic acid (15.4 ml) and a potassium carbonate (32.9 g)/water (150 ml) solution were treated to give crude (2S)-2-(1-phenethylamino)-2-[(4R)-2,2-dimethyl-1,3-dioxolan-4-yl]ethanol (compound [4], 57 g, 1:1 diastereomer mixture) as a yellow oil, which was used in the next step without purification.

EXAMPLE 10

(Production of compound [5]—Step 3)

5% Palladium-carbon (10.0 g) was suspended in an isopropyl alcohol solution, and crude (2S)-2-[(R)-1-phenethylamino]-2-[(4R)-2,2-dimethyl-1,3-dioxolan-4-yl]ethanol (107.4 g) obtained in Example 7 and benzoic acid (46.0 g) were added. The mixture was stirred at 60° C. for 9 hr under a hydrogen atmosphere. Then, the catalyst was filtered off and the filtrate was concentrated under reduced pressure. To the residue was added isopropyl alcohol (53 ml) and the mixture was stirred at 70° C. to dissolve the crystals. n-Heptane (526 ml) was added dropwise at 65° C. and the mixture was cooled to not more than 5° C., which was followed by stirring for one more hour. After filtration, the residue was washed with a 1 wt % isopropyl alcohol/n-heptane solution and dried to give (2S)-2-amino-2-[(4R)-2,2-dimethyl-1,3-dioxolan-4-yl]ethanol benzoate (90.8 g, from compound [3'], yield 85%) as colorless crystals. mp. 112–113° C.

$^1$H-NMR(CDCl$_3$,300 MHz): δ 7.99 (m,2H), 7.44 (m,1H), 7.34 (m,2H), 6.33 (brs,3H), 4.18 (td,1H,J=6.2,7.7 Hz), 4.01 (dd,1H,J=2.2,8.4 Hz), 3.78 (dd,1H,J=3.7, 12.5 Hz), 3.70 (dd,1H,J=5.9,8.8 Hz), 3.63 (dd,1H, J=6.2,12.5 Hz), 1.32 (s,3H), 1.24 (s,3H).

IR(CHCl$_3$) 2983,1610,1517,1393,1214,1080,1048,849, 711,377 cm$^{-1}$; [α]D20+2.50 (c1.00, CHCl$_3$) Anal. Calcd for C$_{14}$H$_{21}$NO$_5$: C,59.35; H,7.47; N,4.94 Found: C,59.11; H,7.65; N,4.98.

EXAMPLE 11

In the same manner as in Example 10, 5% palladium-carbon (5.0 g), crude (2S)-2-benzylamino-2-[(4R)-2,2-dimethyl-1,3-dioxolan-4-yl]ethanol (compound [4], 52 g) obtained in Example 8 and benzoic acid (24.2 g) were treated to give (2S)-2-amino-2-[(4R)-2,2-dimethyl-1,3-dioxolan-4-yl]ethanol benzoate (47.2 g, from compound [3'], yield 84%, 89% ee as yellow crystals). [α]D+2.2° (c1.00, CHCl$_3$)

EXAMPLE 12

In the same manner as in Example 10, 5% palladium-carbon (5.0 g), crude (2S)-2-(1-phenethylamino)-2-[(4R)-2,2-dimethyl-1,3-dioxolan-4-yl]ethanol (compound [4], 57 g, 1:1 diastereomer mixture) obtained in Example 9 and benzoic acid (24.2 g) were treated to give (2S)-2-amino-2-[(4R)-2,2-dimethyl-1,3-dioxolan-4-yl]ethanol benzoate (46.0 g, from compound [3'], yield 82%, 90% ee) as yellow crystals.

[α]D+2.30 (c1.00, CHCl$_3$)

The yield of compound [3'], which does not usually exceed 40%, increased to not less than 40% (57–97%) in Examples 1–4. The reaction proceeded under mild temperature conditions of room temperature to 40° C. In addition, compound [5] was converted to benzoate and could be produced as crystals at high yields (from compound [3'] at yields of 82–85%).

As is evident from the foregoing, the present invention enables stereoselective production of a desired intermediate compound, which is an HIV protease inhibitor, extremely efficiently as compared to conventional methods. The stereoselective synthetic method of the optically active amino alcohol of the present invention is a very useful method which can be used not only for the production of said intermediate compound but also for the production of various other compounds.

This application is based on application No. 6836/1998 filed in Japan, the content of which is incorporated hereinto by reference.

What is claimed is:

1. A method for producing an optically active amino alcohol compound of the formula [3]

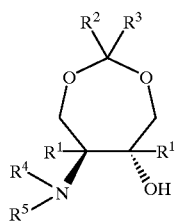

wherein
  $R^1$, $R^2$ and $R^3$ are the same or different and each is a hydrogen atom, an optionally substituted lower alkyl, an optionally substituted aryl or an optionally substituted aralkyl, or $R^1$ and $R^1$ or $R^2$ and $R^3$ in combination form an optionally substituted ring; and
  $R^4$ and $R^5$ are the same or different and each is a hydrogen atom, an optionally substituted lower alkyl, an optionally substituted aryl, an optionally substituted aralkyl or an acyl, or $R^4$ and $R^5$ in combination form an optionally substituted ring together with the adjacent nitrogen atom, or $R^4$ and $R^5$ in combination form an imide group or an azide group together with the adjacent nitrogen atom, an enantiomer thereof or a salt thereof, comprising reacting a mesoepoxide compound of the formula [1]

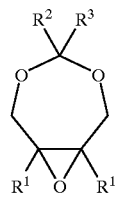

[1]

wherein $R^1$, $R^2$ and $R^3$ are as defined above, with a compound of the formula [2]

[2]

wherein $R^4$ and $R^5$ are as defined above, and $R^6$ is a hydrogen atom or a silyl group, in the presence of a mixed catalyst comprising a Lewis acid and a proton donor.

2. The method of claim 1 for producing an optically active amino alcohol compound of the formula [3']

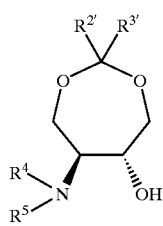

[3']

wherein
  $R^{2'}$ and $R^{3'}$ are the same or different and each is a hydrogen atom, an optionally substituted lower alkyl or an aryl, or $R^{2'}$ and $R^{3'}$ in combination form a cycloalkyl ring together with the adjacent carbon atom; and
  $R^4$ and $R^5$ are the same or different and each is a hydrogen atom, an optionally substituted lower alkyl an optionally substituted aryl, an optionally substituted aralkyl or an acyl, or $R^4$ and $R^5$ in combination form an optionally substituted ring together with the adjacent nitrogen atom, or $R^4$ and $R^5$ in combination form an imide group or an azide group together with the adjacent nitrogen atom, an enantiomer thereof or a salt thereof, comprising reacting a mesoepoxide compound of the formula [1']

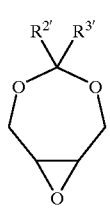

[1']

wherein $R^{2'}$ and $R^{3'}$ are as defined above, with a compound of the formula [2]

[2]

wherein $R^4$ and $R^5$ are as defined above and $R^6$ is a hydrogen atom or a silyl group, in the presence of a mixed catalyst comprising a Lewis acid and a proton donor.

3. A method for producing an optically active 1,3-dioxolane compound of the formula [4]

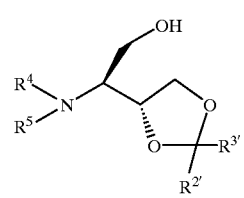

[4]

wherein
  $R^{2'}$ and $R^{3'}$ are the same or different and each is a hydrogen atom, an optionally substituted lower alkyl or an aryl, or $R^{2'}$ and $R^{3'}$ in combination form a cycloalkyl ring together with the adjacent carbon atom; and
  $R^4$ and $R^5$ are the same or different and each is a hydrogen atom, an optionally substituted lower alkyl, an optionally substituted aryl, an optionally substituted aralkyl or an acyl, or $R^4$ and $R^5$ in combination form an optionally substituted ring together with the adjacent nitrogen atom, or $R^4$ and $R^5$ in combination form an imide group or an azide group together with the adjacent nitrogen atom, or an enantiomer thereof, comprising reacting a mesoepoxide compound of the formula [1]

[1']

wherein $R^{2'}$ and $R^{3'}$ are as defined above, with a compound of the formula [2]

[2]

wherein $R^4$ and $R^5$ are as defined above and $R^6$ is a hydrogen atom or a silyl group, in the presence of a mixed catalyst comprising a Lewis acid and a proton donor, to give an optically active amino alcohol compound of the formula [3']

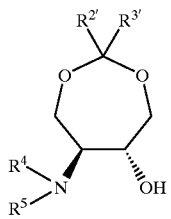

[3']

wherein $R^{2'}$, $R^{3'}$, $R^4$ and $R^5$ are as defined above, an enantiomer thereof or a salt thereof, and isomerizing the resulting compound to a 5-membered ring in the presence of an acid.

4. A method for producing an optically active amino alcohol compound having 1,3-dioxolane, which is represented by the formula [5]

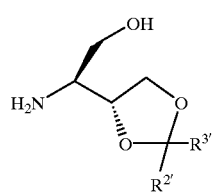

[5]

wherein $R^{2'}$ and $R^{3'}$ are the same or different and each is a hydrogen atom, an optionally substituted lower alkyl or an aryl, or $R^{2'}$ and $R^{3'}$ in combination form a cycloalkyl ring together with the adjacent carbon atom, an enantiomer thereof or a salt thereof, comprising reacting a mesoepoxide compound of the formula [1']

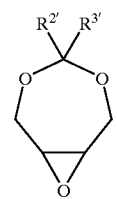

[1']

wherein $R^{2'}$ and $R^{3'}$ are as defined above, with a compound of the formula [2]

[2]

wherein $R^4$ and $R^5$ are the same or different and each is a hydrogen atom, an optionally substituted lower alkyl, an optionally substituted aryl, an optionally substituted aralkyl or an acyl, or $R^4$ and $R^5$ in combination form an optionally substituted ring together with the adjacent nitrogen atom, or $R^4$ and $R^5$ in combination form an imide group or an azide group together with the adjacent nitrogen atom; and $R^6$ is a hydrogen atom or a silyl group, in the presence of a mixed catalyst comprising a Lewis acid and a proton donor, to give an optically active amino alcohol compound of the formula [3']

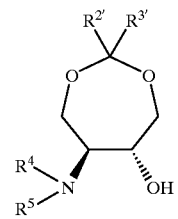

[3']

wherein $R^{2'}$, $R^{3'}$, $R^4$ and $R^5$ are as defined above, an enantiomer thereof or a salt thereof, converting the resulting compound to an optically active 1,3-dioxolane compound of the formula [4]

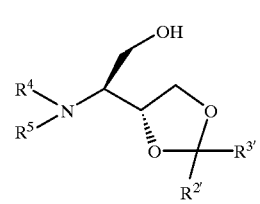

[4]

wherein $R^{2'}$, $R^{3'}$, $R^4$ and $R^5$ are as defined above, or an enantiomer thereof, in the presence of an acid, and eliminating the substituent(s) $R^4$ and/or $R^5$ on the nitrogen atom.

5. The production method of claim 1, wherein the proton donor is at least one member selected from the group consisting of (R)-1,1'-bi-2-naphthol, (S)-1,1'-bi-2-naphthol, catechol and 4-tert-butylcatechol, and the Lewis acid is at least one member selected from the group consisting of titanium tetraisopropoxide, titanium tetrachloride, tin chloride, copper chloride, iron chloride, zinc chloride, zinc bromide, zinc iodide, aluminum chloride, aluminum bromide, alkylaluminum, alkylaluminum chloride, aluminum alkoxide, magnesium chloride, zirconocene, zirconium tetrapropoxide, zirconium chloride, zirconium sulfate, zirconium fluoride, boron bromide, boron chloride and boron fluoride.

6. The production method of claim 3, wherein the proton donor is at least one member selected from the group consisting of (R)-1,1'-bi-2-naphthol, (S)-1,1'-bi-2-naphthol, catechol and 4-tert-butylcatechol, and the Lewis acid is at least one member selected from the group consisting of titanium tetraisopropoxide, titanium tetrachloride, tin chloride, copper chloride, iron chloride, zinc chloride, zinc bromide, zinc iodide, aluminum chloride, aluminum bromide, alkylaluminum, alkylaluminum chloride, aluminum alkoxide, magnesium chloride, zirconocene, zirconium tetrapropoxide, zirconium chloride, zirconium sulfate, zirconium fluoride, boron bromide, boron chloride and boron fluoride.

7. The production method of claim 4, wherein the proton donor is at least one member selected from the group consisting of (R)-1,1'-bi-2-naphthol, (S)-1,1'-bi-2-naphthol, catechol and 4-tert-butylcatechol, and the Lewis acid is at least one member selected from the group consisting of titanium tetraisopropoxide, titanium tetrachloride, tin chloride, copper chloride, iron chloride, zinc chloride, zinc bromide, zinc iodide, aluminum chloride, aluminum bromide, alklaluminum, alkylaluminum chloride, aluminum alkoxide, magnesium chloride, zirconocene, zirconium tetrapropoxide, zirconium chloride, zirconium sulfate, zirconium fluoride, boron bromide, boron chloride and boron fluoride.

8. The production method of claim 1, wherein the proton donor is (R)-1,1'-bi-2-naphthol or (S)-1,1'-bi-2-naphthol, and the Lewis acid is titanium tetraisopropoxide.

9. The production method of claim 3, wherein the proton donor is (R)-1,1'-bi-2-naphthol or (S)-1,1'-bi-2-naphthol, and the Lewis acid is titanium tetraisopropoxide.

10. The production method of claim 4, wherein the proton donor is (R)-1,1'-bi-2-naphthol or (S)-1,1'-bi-2-naphthol, and the Lewis acid is titanium tetraisopropoxide.

11. The production method of claim 2, wherein the proton donor is at least one member selected from the group consisting of (R)-1,1'-bi-2-naphthol, (S)-1,1'bi-2-naphthol, catechol and 4-tert-butylcatechol, and the Lewis acid is at least one member selected from the group consisting of titanium tetraisopropoxide, titanium tetrachloride, tin chloride, copper chloride, iron chloride, zinc chloride, zinc bromide, zinc iodide, aluminum chloride, aluminum bromide, alkylaluminum, alkylaluminum chloride, aluminum alkoxide, magnesium chloride, zirconocene, zirconium tetrapropoxide, zirconium chloride, zirconium sulfate, zirconium fluoride, boron bromide, boron chloride and boron fluoride.

12. The production method of claim 2, wherein the proton donor is (R)-1,1'bi2-naphthol or (S)-1,1'bi-2-naphthol, and the Lewis acid is titanium tetraisopropoxide.

* * * * *